(12) United States Patent
Peng et al.

(10) Patent No.: US 11,835,440 B2
(45) Date of Patent: Dec. 5, 2023

(54) MULTI-CAPILLARY FORCE CURVE AVERAGING METHOD BASED ON MULTI-SAMPLE OVERALL VIRTUAL MEASUREMENT

(71) Applicant: Southwest Petroleum University, Chengdu (CN)

(72) Inventors: Xiaolong Peng, Chengdu (CN); Suyang Zhu, Chengdu (CN); Chaowen Wang, Chengdu (CN); Peng Deng, Chengdu (CN); Chunsheng Jia, Chengdu (CN); Dong Fei, Chengdu (CN); Haoqiang Wu, Chengdu (CN); Zeyu Ye, Chengdu (CN); Si Zhang, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 29 days.

(21) Appl. No.: 17/384,244

(22) Filed: Jul. 23, 2021

(65) Prior Publication Data
US 2022/0412869 A1 Dec. 29, 2022

(30) Foreign Application Priority Data
Jun. 28, 2021 (CN) .......................... 202110720187.2

(51) Int. Cl.
*G01N 15/08* (2006.01)
*G01N 33/24* (2006.01)

(52) U.S. Cl.
CPC ......... *G01N 15/0806* (2013.01); *G01N 33/24* (2013.01)

(58) Field of Classification Search
CPC ..................................................... G01N 33/24
(Continued)

(56) References Cited

U.S. PATENT DOCUMENTS 6,792,354 B1 * 9/2004 O'Meara, Jr. .......... G01V 99/00
702/6

FOREIGN PATENT DOCUMENTS

WO   WO-2017030599 A1 * 2/2017 ........... G01N 15/088

OTHER PUBLICATIONS

Leger et al., "Influence of the wetting angle on capillary forces in pressure filtration," Acta Materialia 91 (Year: 2015).*

* cited by examiner

*Primary Examiner* — Mischita L Henson
(74) *Attorney, Agent, or Firm* — MUNCY, GEISSLER, OLDS & LOWE, PC

(57) ABSTRACT

The present invention relates to a multi-capillary force curve averaging method based on the overall virtual measurement of a plurality of samples. The method includes the following steps: 1, taking m types of rock samples, obtaining a capillary force-saturation curve, an apparent volume and a porosity of each sample; 2, inspecting the quality of the capillary force-saturation curve of each sample and preprocessing the end points of each curve; 3, calculating an averaged wet phase saturation corresponding to different capillary force values of the plurality of samples under the overall virtual measurement of a plurality of samples; and 4, denoting data points on a graph by using the wet phase saturation as the abscissa and capillary force as the ordinate, and finally connecting all data points smoothly to obtain the averaged capillary force curve. This method of the present invention is reliable in principle and easy to operate, can be directly operated on the capillary force curves, is also suitable for various types of samples with different physical properties in consideration of the influence of the numbers of reservoirs represented by samples, has a wide range of applications, and accurate and convenient calculation
(Continued)

results, and is more consistent with actual working conditions.

5 Claims, 3 Drawing Sheets

(58) Field of Classification Search
USPC .......................................................... 702/2
See application file for complete search history.

MULTI-CAPILLARY FORCE CURVE AVERAGING METHOD BASED ON MULTI-SAMPLE OVERALL VIRTUAL MEASUREMENT

TECHNICAL FIELD

The present invention relates to an averaging method for capillary force curves in a process of measuring a capillary force in the fields of oil and gas field development, geotechnical engineering and other seepage mechanics, in particular to an averaging method for multi-capillary force curves where the number of reservoirs represented by samples is different, or J functions are significantly different.

BACKGROUND ART

A capillary force is an important force for the seepage of oil and gas reservoirs, and a capillary force curve is a basic parameter of oil and gas reservoir development. The capillary force is particularly sensitive to a pore size, a pore shape, a pore structure, rock and mineral properties, fluid properties, temperature and pressure, a seepage environment, etc. Therefore, the capillary force curves of different samples generally have obvious differences. Even in the case of the same sample, it is also difficult to obtain the same capillary force curve from different tests, so reservoir engineering often needs to obtain an averaged capillary force curve based on a plurality of capillary force curves. Initially, people used various averaging treatments directly on a plurality of capillary force curves or used a plurality of weighted averaging methods to construct an averaged capillary force-saturation curve (Huang Xinbo. Normalization Method and Application of Averaged Capillary Pressure Curve of Branched Flow Unit [J]. Petroleum Geology and Engineering, 2016, 30(3); Yang Yurui, Guo Xiao, Yang Jianping, et al. New Method for Obtaining Averaged Capillary Pressure Curve of Reservoir [M]. 2018; Li Jing, Chen Peiyuan, Yang Renfeng, et al. Method for Improving Calculation Accuracy of Averaged Capillary Pressure Curve of Low-porosity Sorting Reservoir [M]. 2020).

At present, a J function averaging method is mainly used. First, a capillary force-saturation curve of each sample is converted into a J function of each sample. Then, the J functions are interpolated to obtain an averaged J function. Next, a capillary force is calculated according to a roughly averaged porosity, permeability and fluid interracial tension (Liao Jing, Peng Caizhen, Lu Wenjun, et al. Capillary Pressure Curve Averaging and J Function Processing [J]. Special Oil and Gas Reservoirs, 2008, 15(6)). The limitations of such methods are as follows: (1) these methods are not suitable for the case where different samples have significantly different J functions; (2) J function interpolation lacks strict physical meaning, and since there are many interpolation methods, the results of different methods are quite different, and the construction of interpolation methods has strong subjectivity; and (3) most of these methods cannot consider the influence of the number of samples.

SUMMARY OF THE INVENTION

An objective of the present invention is to provide a multi-capillary force curve averaging method based on the overall virtual measurement of a plurality of samples. This method is reliable in principle and easy to operate, can be directly operated on the capillary force curves, is also suitable for various types of samples with different physical properties in consideration of the influence of the numbers of reservoirs represented by samples, has a wide range of applications, and accurate and convenient calculation results, and is more consistent with actual working conditions.

To fulfill said technical objective, the present invention adopts the following technical solutions.

Since each capillary force curve represents a capillary force-saturation curve of samples of the same category, an averaged curve of a plurality of capillary force curves is understood as a capillary force curve in which a plurality of samples is measured simultaneously, and all the samples obtained are measured simultaneously. Since the capillary force curve of each sample has been measured, the capillary force curves when these samples as a whole are measured can be calculated based on these curves. It can be seen from the principle of experimental measurement of capillary forces: the curve calculated in this way should be the same as an actually measured curve. Therefore, if the capillary force curve of each sample is known, this result can be obtained without actually measuring all samples as a whole, so this method is referred to as multi-sample virtualized overall measurement.

A multi-capillary force curve averaging method based on the overall virtual measurement of a plurality of samples, sequentially comprising the following steps:

1, taking m types of rock samples, obtaining a capillary force-saturation curve $p_c(S_w)$–$S_w$, an apparent volume $V_b$ and a porosity $\phi$ of each sample, and marking the capillary force-saturation curve of a $j^{th}$ sample as $p_c^j(S_w)$–$S_w$, the apparent volume as $V_b^j$ and the porosity as $\phi^j$;

2, inspecting the quality of the capillary force-saturation curve of each sample and preprocessing the end points of each curve, wherein the specific process is as follows:

(1) ensuring that the change in the capillary force Pic of each capillary force-saturation curve $P_c^j(S_w)$–$S_w$ ($\forall j \in \{1,2,\ldots,m\}$) over the saturation $S_w$ satisfies a monotonic function feature;

(2) ensuring that a maximum value of capillary force-saturation curves is greater than a maximum capillary force value $P_{c\ max}$ required by the averaged capillary force-saturation curve;

(3) extrapolating a gentle section of the capillary force-saturation curve to the wet phase saturation $S_w=1$, wherein the corresponding capillary pressure is a displacement pressure; taking the minimum displacement pressure in all samples as $P_{c\ min}$, and replacing the original curve section of the same saturation interval with the curve section obtained by extrapolation; and (4) naming the processed capillary force-saturation curve as $\tilde{P}_c^j(S_w)$–$S_w$;

3, taking a series of enough values at equal intervals or unequal intervals from a real number interval $[P_{c\ min}, P_{c\ max}]$, and denoting them as $\{P_{ci}\}$, $0 \leq i \leq N$, wherein the subscript i represents an $i^{th}$ data point, and $P_{c0}=P_{cmin}$, $P_{cN}=P_{c\ max}$; calculating an averaged wet phase saturation $\overline{S}_{wi}$ corresponding to different capillary force values $P_{ci}$ under the overall virtual measurement of a plurality of samples, wherein the specific process is as follows:

(1) when the capillary force-saturation curve is expressed by an analytical function:

$$P_c = \tilde{P}_c^j(S_w)(j \in \{1,2,\ldots,m\})$$

since the change in the capillary force with saturation satisfies monotonicity, the capillary force-saturation function $\tilde{P}_c^j(S_w)$ has an inverse function:

$$S_w = \text{anti}\tilde{P}_c^j(p_c)$$

calculating the averaged wet phase saturation of a plurality of samples by using the following formula:

$$\bar{S}_{wi} = \frac{\sum_{j=1}^{m} V_b^j \phi^j \text{anti}\tilde{P}_c^j(p_{ci})}{\sum_{j=1}^{m} V_b^j \phi^j} \quad (2)$$

when the capillary force-saturation curve is represented by a graphical curve, finding the corresponding wet phase saturation $S_{wi}^j$ from the capillary force-saturation curve $\tilde{P}_c^j(S_w)$–$S_w$ of each sample j j ∈ {1, 2, . . . , N} for each capillary force value $P_{ci}$ in the sequence—{$P_{ci}$|$P_{ci}$ ∈ [$P_{c\,min}$,$P_{c\,max}$], $P_{c0}=P_{c\,min}$, $P_{cN}=P_{c\,max}$, i ∈ {0, 1, . . . , N}}, and then calculating the averaged wet phase saturation $S_{wi}$ of the plurality of samples according to the following formula:

$$\bar{S}_{wi} = \frac{\sum_{j}^{m} V_b^j \phi^j S_{wi}^j}{\sum_{j}^{m} V_b^j \phi^j} \quad (i \in \{0, 1, \ldots, N\}) \quad (3)$$

when the capillary force-saturation curve $\tilde{P}_c^j(S_w)$–$S_w$ is described with a data table, two processing methods may be adopted: according to a function relationship $p_{ck}^j$~$S_{wk}^j$, k ∈ {1,2, . . . , $N_{tab}^j$}, ($N_{tab}^j$ represents a total number of data points in the capillary force data table of the $j^{th}$ sample) determined based on the data sheet, determining a $P_{ci}$ value $S_{wi}^j$ on the capillary force-saturation curve of the $j^{th}$ sample by using internal interpolation manner; and calculating an averaged wet phase saturation $\bar{S}_{wi}$ of the plurality of samples according to the following formula:

$$\bar{S}_{wi} = \frac{\sum_{j}^{m} V_b^j \phi^j S_{wi}^j}{\sum_{j}^{m} V_b^j \phi^j} \quad (i \in \{0, 1, \ldots, N\}) \quad (4)$$

denoting data points ($\bar{S}_{wi}$, $p_{ci}$) on the graph by using the wet phase saturation $\bar{S}_{wi}$ as the abscissa and capillary force $P_{ci}$ as the ordinate, and finally connecting all data points smoothly to obtain the averaged capillary force curve.

In the step 2, ensuring that a maximum value of all capillary force-saturation curves is greater than a maximum capillary force value $P_{c\,max}$ required by the averaged capillary force-saturation curve means to extending an end point curve of the capillary force-saturation curve that does not meet the requirements by an extrapolation method until the maximum capillary force value of the capillary force-saturation curves exceeds $P_{c\,max}$.

In the step 3, when the capillary force-saturation curve is represented with a graphic curve or described with a data table, if Pu is less than the minimum capillary force value on the capillary force-saturation curve $\tilde{P}_c^j(S_w)$–$S_w$ of the $j^{th}$ sample, $S_{wi}^j$=1 is taken.

In the step 3, when the capillary force-saturation curve) ($\tilde{P}_c^j(S_w)$–$S_w$) is described with a data table, a graph of capillary force-saturation curve is drawn according to these data points, and converted to a case (2) for processing.

In the step 3, when the capillary force-saturation curve is expressed in a mixed way of function, graph and data table description, the averaged wet phase saturation $S_{wi}^j$ is obtained respectively according to the cases (1) to (3) in the step.

Compared with the prior art, the present invention has the following technical effects:

(1) operations are performed directly on the capillary force curves, while a mainstream method first converts the capillary force curve into a J function curve, and the J function curves are then averaged by interpolation or other methods;

(2) this method can take the influence of the number of reservoirs represented by samples into consideration, while the mainstream method generally cannot take the influence of the number of samples into consideration;

(3) this method is also suitable for various types of samples with different physical properties; even if the capillary force curves of different samples are greatly different, a unique averaged capillary force curve can also be obtained; even if the J functions of the reservoirs are different, and even quiet different, the only averaged capillary force curve can be obtained; and (4) this method has a clear physical meaning.

a is capillary force curves respectively measured for a sample α and a sample β; b is capillary force curves obtained by taking the sample α and the sample β into an instrument together for overall measurement; and c is a capillary force curve obtained by taking different numbers of sample α and sample β into the instrument for overall measurement.

Figure 2:
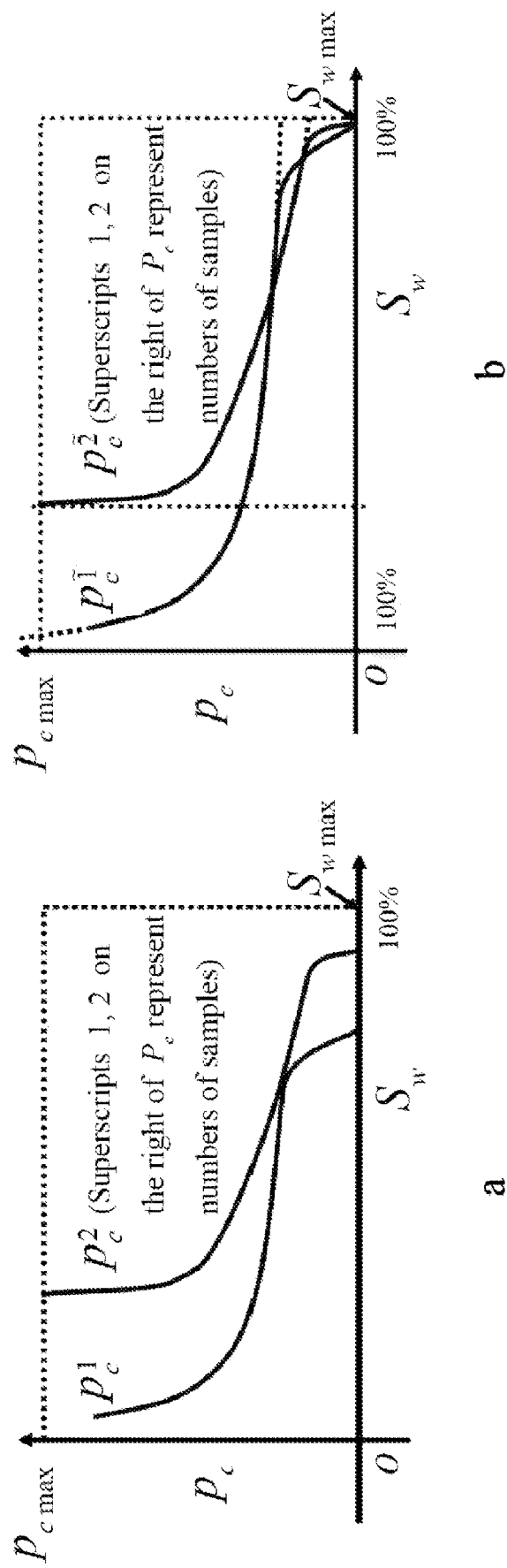

FIG. 2 is a schematic diagram of preprocessing of end points of a capillary force curve.

a is an original capillary force curve; b is a curve after the capillary force curve is extended at the end points.

Figure 3:
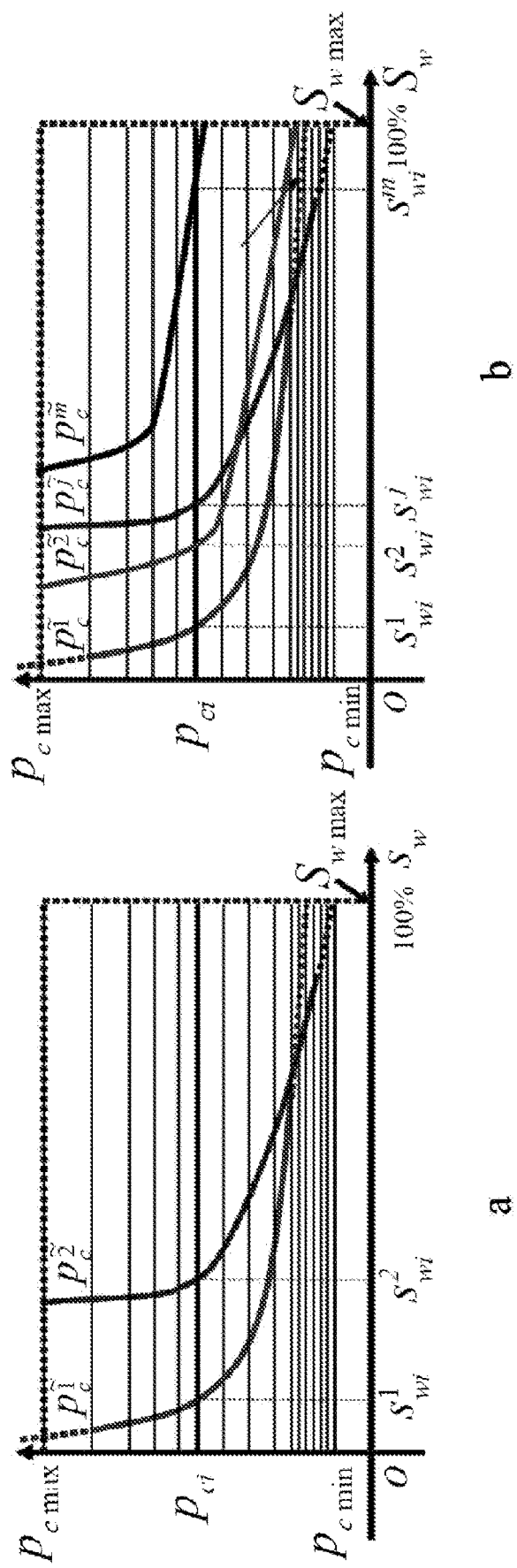

FIG. 3 shows a corresponding wet phase saturation ($S_{wi}^j$) for different capillary forces ($P_{ci}$) by different capillary force curves ($P_c^i$–$S_w$).

a is a schematic diagram of two types of sample curves; and b is a schematic diagram of m type of samples.

DETAILED DESCRIPTION

To facilitate those skilled in the art to understand the present invention, the present invention will be further described below according to the accompanying drawings. However, it should be clear that the present invention is not limited to the scope of the specific embodiments. For those of ordinary skill in the art, as long as various changes fall within the spirit and scope of the present invention defined and determined by the appended claims, they are all protected.

In the present invention, the subscript w represents a wet phase fluid; the subscript n represents a non-wet phase fluid; $P_c$ represents a capillary force; S represents a saturation; $S_w$ represents a wet phase saturation; $V_b$ represents an apparent volume of a rock sample; and φ represents a porosity of a sample. A variable m represents the number of samples; the superscript j represents a $j^{th}$ sample.

Figure 1:
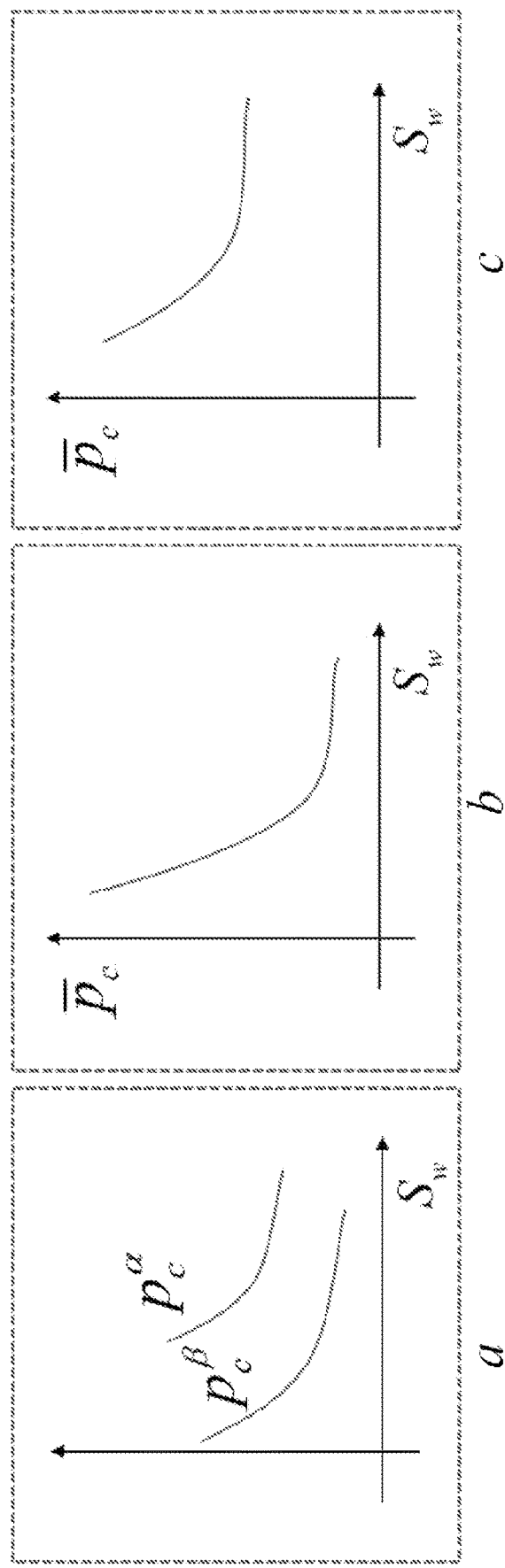
FIG. 1 is a schematic diagram of a multi-capillary force curve averaging method based on multi-sample overall measurement.

Referring to FIG. 1, taking an oil-water two-phase capillary force as an example, if there are two samples α and β, capillary force curves measured respectively by experiments are: $p_c^\alpha(S_w)$–$S_w$, $p_c^\beta(S_w)$–$S_w$, the averaged capillary force is equivalent to putting the two samples into the instruction at the same time for measurement. In FIG. 1, a is capillary force curves $p_c^\alpha$–$S_w$, $p_c^\beta$–$S_w$ respectively measured for the sample α and the sample β; b is capillary force curves $\overline{P}_c$–$S_w$ obtained by taking the sample α and the sample β into an instrument together for overall measurement; and c is a capillary force curve $\overline{P}_c$–$S_w$ obtained by taking different numbers of sample α and sample β into the instrument for overall measurement.

The multi-capillary force curve averaging method based on the overall virtual measurement of a plurality of samples sequentially comprises the following steps:

1, taking m types of rock samples, obtaining a capillary force-saturation curve $p_c(S_w)$–$S_w$, an apparent volume $V_b$ and a porosity ϕ of each sample, and marking the capillary force-saturation curve of the $j^{th}$ sample as $p_c^j(S_w)$–$S_w$, the apparent volume $V_b^j$ as and the porosity as $\phi^j$;

2, inspecting the quality of the capillary force-saturation curve of each rock sample and preprocessing the end points of each capillary force-saturation curve (as shown in FIG. 2), and the specific process is as follows:
  (1) ensuring that the change in the capillary force $P'_c$ of each capillary force-saturation curve $p_c(S_w)$–$S_w$ ($\forall j \in \{1,2,\ldots,m\}$) over the saturation $S_w$ satisfies a monotonic function feature; otherwise indicating that the quality of the capillary force-saturation curve is unqualified and needs to be corrected;
  (2) ensuring that a maximum value of all capillary force-saturation curves is greater than a maximum capillary force value $P_{c\ max}$ required by the averaged capillary force-saturation curve; otherwise, extending an end point curve of the capillary force-saturation curve that does not meet the requirements by an extrapolation method until the maximum capillary force value of the capillary force-saturation curves exceeds $P_{c\ max}$;
  (3) extrapolating a gentle section of the capillary force-saturation curve to the wet phase saturation $S_w$=1, wherein the corresponding capillary pressure is a displacement pressure; taking the minimum displacement pressure in all samples as $P_{c\ min}$, and replacing the original curve section of the same saturation interval with the curve section obtained by extrapolation; and
  (4) naming the processed capillary force-saturation curve as $\tilde{P}_c^j(S_w)$–$S_w$ (corresponding to the capillary force-saturation curve $P_c^j(S_w)$–$S_w$ before processing);

3, taking a series of enough values at equal intervals or unequal intervals from a real number interval [$P_{c\ min}$, $P_{c\ max}$], and denoting them as {$p_{ci}$}, 0≤i≤N, wherein the subscript i represents an $i^{th}$ data point, and $p_{c0}$=$p_{c\ min}$, $p_{cN}$=$p_{c\ max}$; calculating an averaged wet phase saturation corresponding to different capillary force values $P_{ci}$ under the overall virtual measurement of a plurality of samples (this saturation can be understood as a type of weighted average saturation), and denoting it as $\overline{S}_{wi}$, wherein the specific process is as follows:

considering that there are four ways to express the capillary force-saturation curves in practice, that is, a. analytical formula method; b. graphic method; c. data table; d. hybrid method, the present invention is also divided into four methods for processing:
  (1) when the capillary force-saturation curve is expressed by an analytical function:

$$p_c = \tilde{P}_c^j(S_w) (j \in \{1,2,\ldots,m\}) \qquad (1)$$

since the change in the capillary force with saturation satisfies monotonicity, the capillary force-saturation function $\tilde{P}_c^j(S_w)$ has an inverse function, denoted as:

$$S_w = \text{anti}\tilde{P}_c^j(p_c) \qquad (2)$$

calculating the averaged wet phase saturation of a plurality of samples by using the following formula:

$$\overline{S}_{wi} = \frac{\sum_{j=1}^{m} V_b^j \phi^j \text{anti}\tilde{P}_c^j(p_{ci})}{\sum_{j=1}^{m} V_b^j \phi^j} \qquad (3)$$

substituting all $P_{ci}$ into Formula (3) sequentially, to calculate the corresponding averaged wet phase saturation $\overline{S}_{wi}$;

(2) when the capillary force-saturation curve is represented by a graphical curve, finding the corresponding wet phase saturation from the capillary force-saturation curve $\tilde{P}_c^j(S_w)$–$S_w$ of each sample j ∈ {1,2,..., N} for each capillary force value $P_{ci}$ in the sequence {$P_{ci}$|$P_{ci}$∈ [$P_{c\ min}$, $P_{c\ max}$], $P_{c0}$=$P_{c\ min}$, $P_{cN}$=$P_{c\ max}$ i∈ {0, 1,..., N}}, and denoting it as $S^j_{wi}$, and then calculating the averaged wet phase saturation $S_{wi}$ of the plurality of samples according to the following formula:

$$\overline{S}_{wi} = \frac{\sum_{j}^{m} V_b^j \phi^j S_{wi}^j}{\sum_{j}^{m} V_b^j \phi^j} \quad (i \in \{0, 1, \ldots, N\}) \qquad (4)$$

if certain P is less than a minimum capillary force value min($\tilde{P}_c^j(S_w)$), ($S_{wi}$≤$S_w$≤1) on the capillary force-saturation curve $\tilde{P}_c^j(S_w)$–$S_w$ of the $j^{th}$ sample, taking $S^j_{wi}$=1 (as shown in FIG. 3);

(3) when the capillary force-saturation curve $\tilde{P}_c^j(S_w)$–$S_w$ is described with a data table, two processing methods may be adopted:

1) drawing a graph of capillary force-saturation curve according to these data points, and converting it to a case (2) for processing; 2) according to a function relationship $p_{ck}^j$~$S_{wk}^j$, k ∈ {1,2,..., $N_{tab}^j$}, $N_{tab}^j$ represents a total number of data points in the capillary force data table of the $j^{th}$ sample) determined based on the data sheet of each sample, determining a $P_{ci}$ value on the capillary force-saturation curve of the $j^{th}$ sample by using internal interpolation manner, and denoting said value as $S^j_{wi}$; and calculating an averaged wet phase saturation $\overline{S}_{wi}$ of the plurality of samples according to Formula (4), wherein if certain P is less than the minimum capillary force value min($\tilde{P}_c^j(S_w)$), ($S_{wi}$≤$S_w$≤1) on the capillary force-saturation curve $\tilde{P}_c^j(S_w)$–$S_w$ of the $J^{th}$ sample, taking $S^j_{wi}$=1 directly (as shown in FIGS. 3); and (4) when the capillary force-saturation curve is expressed in a mixed way of function, graph and data table description, obtaining the averaged wet phase saturation $\overline{S}_{wi}$ of the plurality of samples respectively according to the cases (1) to (3) in this step; and 4, denoting data points ($\overline{S}_{wi}$, $p_{ci}$) on the graph by using the wet phase saturation $\overline{S}_{wi}$ as the abscissa and capillary force $P_{ci}$ as the ordinate, and finally connecting all data points smoothly to obtain the averaged capillary force curve.

What is claimed:

1. A multi-capillary force curve averaging method based on the overall virtual measurement of a plurality of samples, sequentially comprising the following steps:

1, taking m types of rock samples, put the m types of rock samples into an experimental instrument and measure the m types of rock samples to obtain a capillary pressure-saturation curve $p_c(S_w)$–$S_w$, an apparent volume $V_b$, and a porosity $\phi$ of each sample, and marking the capillary pressure-saturation curve of $j^{th}$ sample as $p_c^j(S_w)$–$S_w$, the apparent volume as $V_b^j$ and the porosity as $\phi^j$;

2, inspecting the quality of the capillary pressure-saturation curve of each sample and preprocessing the end points of each curve, wherein the specific process is as follows:

(1) ensuring that the change in the capillary pressure $p_c^j$ of each $P_c^j(S_w)$–$S_w$ ($\forall j \in \{1,2,\ldots,m\}$) over the saturation $S_w$ satisfies a monotonic function feature;

(2) ensuring that a maximum value of capillary pressure-saturation curves is greater than a maximum capillary pressure value $p_{c\,max}$ required by the averaged capillary pressure-saturation curve;

(3) extrapolating a gentle section of the capillary pressure-saturation curve to the wet phase saturation $S_w = 1$, wherein the corresponding capillary pressure is a displacement pressure; taking the minimum displacement pressure in all samples as $p_{c\,min}$, and replacing the original curve section of the same saturation interval with the curve section obtained by extrapolation; and (4) naming the processed capillary pressure-saturation curve as $\tilde{P}_c^j(S_w)$–$S_w$;

3, taking a series of enough values at equal intervals or unequal intervals from a real number interval [$p_{c\,min}$, $p_{c\,max}$], and denoting them as $\{p_{ci}\}$, $0 \leq i \leq N$, wherein the subscript i represents an $i^{th}$ data point, and $p_{c0} = p_{c\,min}$, $p_{cN} = p_{c\,max}$; calculating an averaged wet phase saturation $\overline{S}_{wi}$ corresponding to different capillary pressure values $P_{ci}$ under the overall virtual measurement of a plurality of samples, wherein the specific process is as follows:

(1) when the capillary pressure-saturation curve is expressed by an analytical function:

$$p_c = \tilde{P}_c^j(S_w)(j \in \{1,2,\ldots,m\})$$

since the change in the capillary pressure with saturation satisfies monotonicity, the capillary pressure-saturation function $\tilde{P}_c^j(S_w)$ has an inverse function:

$$S_w = \text{anti}\tilde{P}_c^j(p_c)$$

calculating the averaged wet phase saturation of a plurality of samples by using the following formula:

$$\overline{S}_{wi} = \frac{\sum_{j=1}^{m} V_b^j \phi^j \text{anti}\tilde{P}_c^j(p_{ci})}{\sum_{j=1}^{m} V_b^j \phi^j} \quad (2)$$

when the capillary pressure-saturation curve is represented by a graphical curve, finding the corresponding wet phase saturation $S_{wi}^j$ from the capillary pressure-saturation curve $\tilde{P}_c^j(S_w)$–$S_w$ of each sample $j \in \{1, 2, \ldots, m\}$ for each capillary pressure value $P_{ci}$ in the sequence $$\{P_{ci} | P_{ci} \in [P_{c\,min}, P_{c\,max}], P_{c0} = P_{c\,min}, P_{cN} = P_{c\,max}, i \in \{0,1,\ldots,N\}\},$$

and then calculating the averaged wet phase saturation $\overline{S}_{wi}$ of the plurality of samples according to the following formula:

$$\overline{S}_{wi} = \frac{\sum_{j}^{m} V_b^j \phi^j S_{wi}^j}{\sum_{j}^{m} V_b^j \phi^j} \quad (i \in \{0,1,\ldots,N\}) \quad (3)$$

when the capillary pressure-saturation curve ($\tilde{P}_c^j(S_w)$–$S_w$) is described with a data table, two processing methods may be adopted: according to a function relationship $p_{ck}^j \sim S_{wk}$, $k \in \{1,2,\ldots,N_{tab}^j\}$, $N_{tab}^j$ represents a total number of data points in the capillary pressure data table of the $j^{th}$ sample) determined based on the data sheet, determining a $P_{ci}$ value $S_{wi}^j$ on the capillary pressure-saturation curve of the $j^{th}$ sample by using internal interpolation manner; and calculating an averaged wet phase saturation $\overline{S}_{wi}$ of the plurality of samples according to the following formula:

$$\overline{S}_{wi} = \frac{\sum_{j}^{m} V_b^j \phi^j S_{wi}^j}{\sum_{j}^{m} V_b^j \phi^j} \quad (i \in \{0,1,\ldots,N\}) \quad (4)$$

denoting data points ($\overline{S}_{wi}$, $p_{ci}$) on the graph by using the wet phase saturation $\overline{S}_{wi}$ as the abscissa and capillary pressure $P_{ci}$ as the ordinate, and finally connecting all data points smoothly to obtain the averaged capillary pressure curve.

2. The multi-capillary force curve averaging method based on the overall virtual measurement of a plurality of samples according to claim 1, wherein in the step 2, ensuring that a maximum value of all capillary pressure-saturation curves is greater than a maximum capillary pressure value $p_{c\,max}$ required by the averaged capillary pressure-saturation curve means to extending an end point curve of the capillary pressure-saturation curve that does not meet the requirements by an extrapolation method until the maximum capillary pressure value of the capillary pressure-saturation curves exceeds $p_{c\,max}$.

3. The multi-capillary force curve averaging method based on the overall virtual measurement of a plurality of samples according to claim 1, wherein in the step 3, when the capillary pressure-saturation curve is represented with a graphic curve or described with a data table, if $P_{ci}$ is less than the minimum capillary pressure value on the capillary pressure-saturation curve $\tilde{P}_c^j(S_w)$–$S_w$ of the $j^{th}$ sample, $S_{wi}^j=1$ is taken.

4. The multi-capillary force curve averaging method based on the overall virtual measurement of a plurality of samples according to claim 1, wherein in the step 3, when the capillary pressure-saturation curve $\tilde{P}_c^j(S_w)$–$S_w$ is described with a data table, a graph of capillary pressure-saturation curve is drawn according to these data points, and converted to a case (2) for processing.

5. The multi-capillary force curve averaging method based on the overall virtual measurement of a plurality of samples according to claim 1, wherein in the step 3, when the capillary pressure-saturation curve is expressed in a mixed way of function, graph and data table description, the averaged wet phase saturation $\overline{S}_{wi}$ is obtained respectively according to the cases (1) to (3) in the step.

\* \* \* \* \*